United States Patent [19]

Wenk et al.

[11] Patent Number: 4,514,415
[45] Date of Patent: Apr. 30, 1985

[54] BENZOFURAN-2(3H)-ONES USED AS ANTI-INFLAMMATORY AGENTS

[75] Inventors: Paul Wenk, Allschwil; Werner Breitenstein; Marcus Baumann, both of Basel, all of Switzerland

[73] Assignee: Ciba Geigy Corporation, Ardsley, N.Y.

[21] Appl. No.: 435,594

[22] Filed: Oct. 21, 1982

[30] Foreign Application Priority Data

Oct. 28, 1981 [CH] Switzerland .................. 6881/81

[51] Int. Cl.³ .................. C07D 307/83; A61K 31/365
[52] U.S. Cl. .................... 514/470; 549/307; 549/466
[58] Field of Search ............... 549/307, 466; 424/279, 424/285

[56] References Cited

U.S. PATENT DOCUMENTS 3,424,796  1/1969  Galantay et al. .................. 549/307
3,862,133  1/1975  Layer .................................. 549/307
4,013,690  3/1977  Closse et al. ...................... 549/307

FOREIGN PATENT DOCUMENTS 2608697  9/1976  Fed. Rep. of Germany ...... 549/307
50-124930 10/1975  Japan ................................. 549/307
1284282  8/1972  United Kingdom .
1494773 12/1977  United Kingdom .

OTHER PUBLICATIONS

Chem. Abs., vol. 47, 8693 f and 8694 h.

Primary Examiner—Jane T. Fan
Attorney, Agent, or Firm—Michael W. Glynn

[57] ABSTRACT

The invention relates to novel lactones, especially benzofuranones of the general formula

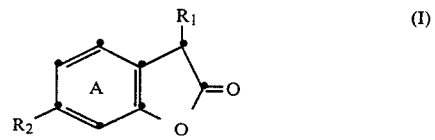

in which $R_1$ represents hydrogen or an aliphatic radical, $R_2$ represents an amino group di-substituted by two monovalent hydrocarbon radicals, and the aromatic ring A may be additionally substituted, and their salts and/or isomers, processes for the manufacture of compounds of the formula (I) and their salts and isomers, pharmaceutical preparations containing these compounds, and their use as the active ingredients of medicaments and/or for the manufacture of pharmaceutical preparations.

11 Claims, No Drawings

BENZOFURAN-2(3H)-ONES USED AS ANTI-INFLAMMATORY AGENTS

The invention relates to novel lactones, especially benzofuranones of the general formula

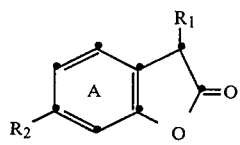

in which $R_1$ represents hydrogen or an aliphatic radical, $R_2$ represents an amino group di-substituted by two monovalent hydrocarbon radicals, and the aromatic ring A may be additionally substituted, and their salts and/or isomers, processes for the manufacture of compounds of the formula (I) and their salts and isomers, pharmaceutical preparations containing these compounds, and their use as the active ingredients of medicaments and/or for the manufacture of pharmaceutical preparations.

Isomers of compounds of the formula (I) are, for example, the 2-hydroxybenzo[b]furan compounds of the formula

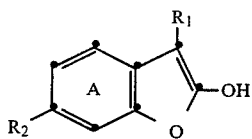

which are in tautomeric equilibrium with the 2,3-dihydro-2-oxobenzo[b]furan derivatives of the formula (I).

An aliphatic radical $R_1$ is, especially, saturated and unsubstituted and represents, especially, a lower alkyl radical.

The aromatic ring A may be additionally mono- or poly-substituted by an aliphatic radical, such as lower alkyl, hydroxy-lower alkyl, halo-lower alkyl, lower alkenyl, or optionally branched, especially bridging two adjacent carbon atoms, 3- or 4-membered alkylene having from 3 to 8 carbon atoms, lower alkoxy, lower alkylthio, lower alkanesulphinyl, lower alkanesulphonyl, hydroxy, halogen, lower alkanoyloxy, lower alkanoyl and/or nitro, or, except for $R_2$, it may be unsubstituted.

An amino group di-substituted by two monovalent hydrocarbon radicals has, as those radicals, monovalent aliphatic radicals, such as lower alkyl radicals, which may be unsubstituted or substituted by 3- to 7-membered cycloalkyl or by aryl, such as unsubstituted phenyl or phenyl substituted by an aliphatic radical, such as lower alkyl, lower alkenyl, lower alkylene, hydroxy-lower alkyl, halogen-lower alkyl, lower alkoxy, lower alkylthio, lower alkanesulphinyl, lower alkanesulphonyl, hydroxy, halogen, lower alkanoyloxy, lower alkanoyl and/or nitro. $R_2$ preferably represents di-lower alkyl-amino, di-cycloalkyl-lower alkylamino, cycloalkyl-lower alkyl-lower alkylamino, di-phenyl-lower alkylamino or lower alkyl-phenyl-lower alkylamino, furthermore phenyl-lower alkyl-cycloalkyl-lower alkylamino.

Hereinbefore and hereinafter, organic radicals and compounds designated "lower" should preferably be understood as being those that contain up to and including 7, especially up to and including 4, carbon atoms.

The general definitions used within the framework of the present text have, especially, the following meanings:

Lower alkyl is, for example, methyl, ethyl, n-propyl, isopropyl, n-butyl, isobutyl, sec.-butyl, tert.-butyl and also includes, correspondingly, pentyl, hexyl and heptyl radicals.

Hydroxy-lower alkyl is, for example, hydroxymethyl, 2-hydroxyethyl or 2- or 3-hydroxypropyl.

Halo-lower alkyl is, for example, chloromethyl or trifluoromethyl.

Lower alkenyl is, for example, vinyl, 1- or 2-propenyl, 1-, 2- or 3-butenyl or butadien-1,3-yl.

3- or 4-membered alkylene is straight-chained, such as tri- or tetra-methylene, or branched, such as 2,4-butylene, 1,4- or 2,4-pentylene or 2-methyl-1,3-propylene.

Lower alkoxy is, for example, methoxy, ethoxy, n-propoxy, isopropoxy, n-butoxy, isobutoxy, sec.-butoxy, tert.-butoxy and also includes, correspondingly, pentyloxy, hexyloxy and heptyloxy radicals.

Lower alkylthio is, for example, methyl-, ethyl-, n-propyl-, isopropyl-, n-butyl-, isobutyl-, sec.-butyl- or tert.-butyl-thio.

Lower alkane-sulphinyl or -sulphonyl is, for example, methane-, ethane-, n-propane- or isopropanesulphinyl or -sulphonyl.

Halogen is, for example, halogen having an atomic number of up to and including 35, such as fluorine, chlorine or bromine, and also includes iodine.

Lower alkanoyloxy is, for example, acetoxy, propionyloxy, butyryloxy, isobutyryloxy, sec.- or tert.-butyryloxy.

Lower alkanoyl is, for example, acetyl, propionyl, butyryl, isobutyryl or tert.-butyryl.

3- to 7-membered cycloalkyl is, for example, cyclopropyl, cyclobutyl, cyclopentyl, cyclohexyl or cycloheptyl.

Salts of compounds of the formula (I) according to the invention are preferably pharmaceutically acceptable salts, such as pharmaceutically acceptable acid addition salts. These are formed, for example, with strong inorganic acids, such as mineral acids, for example sulphuric acid, phosphoric acid, or hydrohalic acids, with strong organic carboxylic acids, such as lower alkanecarboxylic acids, for example acetic acid, such as optionally unsaturated dicarboxylic acids, for example oxalic, malonic, maleic or fumaric acid, or such as hydroxycarboxylic acids, for example tartaric acid or citric acid, or with sulphonic acids, such as lower alkane- or optionally substituted benzene-sulphonic acids, for example methane- or p-toluene-sulphonic acid. If the 1,2-phenylene radical Ph has hydroxy as substituent, corresponding compounds can form salts with bases. Suitable salts with bases are, for example, corresponding alkali metal or alkaline earth metal salts, for example sodium, potassium, or magnesium salts, and pharmaceutically acceptable transition metal salts, such as zinc or copper salts.

Isomers of the formula (I) are especially in the form of structural isomers. If, for example, compounds of the formula (I) have chiral carbon atoms, they may be in the form of diastereoisomers, diastereoisomeric mixtures, or racemates or in the form of a pure enantiomer, while the tautomer forms of the formula (I') form, for example, geometric isomers, for example E/Z isomers.

The compounds of the formula (I) have valuable pharmacological properties. They have, especially, a pronounced anti-inflammatory action which can be demonstrated, for example, by reduction of the carrageenin-induced paw oedema in rats at a dose of approximately 0.1 mg/kg p.o. and above analogously to the methodology described by Pasquale et al, Agents and Actions, 5, 256 (1975), and in the adjuvant-arthritis model in rats at a dose of approximately 1.0 mg/kg p.o. and above analogously to the method described by L. Riesterer and R. Jacques, Pharmacology, 2, 288 (1969). In addition, compounds of the formula (I) inhibit, in vitro, at a concentration of approximately 10 μmol/l and above prostaglandin synthesis from arachidonic acid analogously to the method described by H. L. White and A. T. Glassman, Prostaglandins, 7, 123 (1974).

The compounds of the formula (I) also have an antinociceptive activity that can be derived, for example, from the reduction of the phenyl-p-benzoquinone-induced writhing syndrome in mice at a dose of approximately 0.1 mg/kg p.o. and above. [Methodology: analogous to the method described by L. C. Hendershot and J. Forsaith, J. Pharmacol. exp. Therap. 125, 237 (1959)].

Furthermore, the compounds of the formula (I) have the ability to absorb from the range of the UV spectrum the rays producing erythema on the epidermis (between 290 and 320 nm) while the substances are transmitted by the tanning rays of approximately from 320 to 400 nm.

Consequently, these compounds can be used as anti-inflammatory agents, (peripheral) analgesics and/or light-screening agents, for example for cosmetic purposes.

The invention relates, for example, to compounds of the formula (I) in which $R_1$ represents hydrogen or a saturated aliphatic radical, $R_2$ represents an amino group di-substituted by two monovalent aliphatic radicals which may be unsubstituted or substituted by 3- to 7-membered cycloalkyl or aryl, and the aromatic ring A is additionally mono- or poly-substituted by an aliphatic radical, lower alkoxy, lower alkylthio, lower alkanesulphinyl, lower alkanesulphonyl, hydroxy, halogen, lower alkanoyloxy, lower alkanoyl and/or nitro, or, except for $R_2$, is unsubstituted, and their salts, especially pharmaceutically acceptable salts, and isomers.

The invention relates, for example, to compounds of the formula (I) in which $R_1$ represents hydrogen or lower alkyl, $R_2$ represents a di-lower alkylamino group, a dicycloalkyl-lower alkylamino group having from 3 to 7 ring members in each cycloalkyl moiety, or a diphenyl-lower alkylamino group each phenyl moiety of which is unsubstituted or substituted by lower alkyl, lower alkoxy, hydroxy, halogen, lower alkanoyloxy and/or trifluoromethyl, and the aromatic ring A may be additionally substituted by lower alkyl, lower alkoxy, hydroxy, halogen, lower alkanoyloxy, 3- or 4-membered alkylene and/or trifluoromethyl, and their salts, especially pharmaceutically acceptable salts, and isomers.

The invention relates especially to compounds of the formula

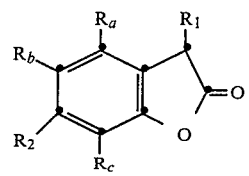

in which $R_1$ represents, on the one hand, hydrogen or, on the other hand, lower alkyl, especially having up to and including 4 carbon atoms, such as methyl, and, in each case, $R_2$ represents di-lower alkylamino, especially having up to and including 4 carbon atoms in each lower alkyl moiety, such as dimethylamino, dicycloalkyl-lower alkylamino having from 3 to 7 ring members in each cycloalkyl moiety and having, especially, up to and including 4 carbon atoms in the lower alkyl moiety, such as dicyclopropylmethylamino, or diphenyl-lower alkylamino which has, especially, up to and including 4 carbon atoms in the lower alkyl moiety, such as dibenzylamino, and each phenyl moiety of which is unsubstituted or substituted by lower alkyl, especially having up to and including 4 carbon atoms, such as methyl, lower alkoxy, especially having up to and including 4 carbon atoms, such as methoxy, hydroxy, halogen, especially having an atomic number of up to and including 35, such as chlorine, lower alkanoyloxy, especially having up to and including 5 carbon atoms, such as acetoxy, and/or by trifluoromethyl, and $R_a$, $R_b$ and $R_c$ each represents, independently of one another hydrogen, lower alkyl, especially having up to and including 4 carbon atoms, such as methyl, lower alkoxy, especially having up to and including 4 carbon atoms, such as methoxy, hydroxy, halogen, especially having an atomic number of up to and including 35, such as chlorine, lower alkanoyloxy, especially having up to and including 5 carbon atoms, such as acetoxy, or trifluoromethyl, and their salts, especially pharmaceutically acceptable salts, and isomers.

The invention relates more especially to compounds of the formula (Ia) in which $R_1$ represents hydrogen, $R_2$ represents di-lower alkylamino having up to and including 4 carbon atoms in each lower alkyl moiety, such as dimethylamino, $R_a$ and $R_c$ represent hydrogen and $R_b$ represents lower alkyl having up to and including 4 carbon atoms, such as methyl, or halogen having an atomic number of up to and including 35, such as chlorine, and their salts, especially pharmaceutically acceptable salts, and isomers.

The invention relates more especially to compounds of the formula (Ia) in which $R_1$ represents lower alkyl having up to and including 4 carbon atoms, such as methyl, $R_2$ represents di-lower alkylamino having up to and including 4 carbon atoms in each lower alkyl moiety, such as dimethylamino or N-methyl-N-(2-butyl)-amino, and $R_a$ and $R_c$ represent hydrogen and $R_b$ represents lower alkyl, having up to and including 4 carbon atoms, such as methyl, or halogen having an atomic number of up to and including 35, such as chlorine, and their salts, especially pharmaceutically acceptable salts, and isomers.

The invention relates especially to the novel compounds mentioned in the Examples, their salts, especially pharmaceutically acceptable salts, and isomers, and also to the processes for their manufacture described in the Examples.

The compounds of the present invention are manufactured in a manner known per se, for example by (a) cyclising a compound of the formula

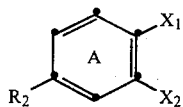 (II)

or a salt thereof, in which $X_1$ represents a group of the formula $-CH(R_1)-X_3$ and $X_3$ represents carboxy or functionally modified carboxy and $X_2$ represents hydroxy or functionally modified hydroxy, or in which $X_1$ represents hydrogen and $X_2$ represents a group of the formula $-O-CO-CH(R_1)-X_4$ in which $X_4$ represents hydroxy or functionally modified hydroxy, or (b) in a compound of the formula

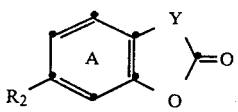 (III)

or a salt or isomer thereof, in which Y represents a radical that can be converted into the groups of the formula $>CH(R_1)$, converting Y into the group of the formula $>CH(R_1)$, or (c) in a compound of the formula

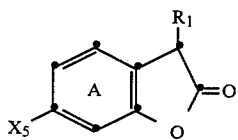 (IV)

or a salt or isomer thereof, in which $X_5$ represents a group that can be converted into $R_2$, converting $X_5$ into $R_2$, or (d) in a compound of the formula

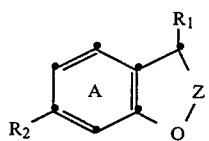 (V)

or a salt thereof, in which Z represents a group that can be converted into the carbonyl group, converting Z into the carbonyl group, or (e) in a compound of the formula

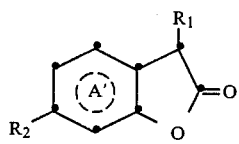 (VI)

or a salt thereof, in which the ring A' is a ring that can be converted into the ring A, converting the ring A' into the ring A, and/or, if desired, converting a salt obtainable according to the process into the free compound or into a different salt, converting a free compound obtainable according to the process into a different free compound or into a salt and/or, if desired, separating an isomeric mixture obtainable according to the process into its components.

Re variant (a):

Starting materials of the formula II may be in the form of salts, for example acid addition salts, or, if the group $X_3$ contains carboxy or the aromatic ring A contains hydroxy, they may be in the form of salts with bases.

Functionally modified carboxy $X_3$ represents, especially, functionally modified carboxy containing an oxo group, such as esterified, amidated or anhydridised carboxy, also an orthocarboxylic acid ester grouping, an orthoanhydride grouping or optionally functionally modified thiocarboxy. Esterified carboxy should be understood as meaning carboxy esterified, for example, by an optionally substituted alcohol, such as optionally substituted alkanol or cycloalkanol, for example lower alkanol or 4- to 7-membered cycloalkanol, or by an optionally substituted phenyl, such as lower alkoxycarbonyl, for example ethoxycarbonyl, cycloalkoxycarbonyl, for example cyclohexyloxycarbonyl, or phenoxycarbonyl. Anhydridised carboxy is, for example, a symmetric or mixed anhydride with inorganic acids, such as hydrohalic acids, or with organic carboxylic acids, such as optionally substituted lower alkanecarboxylic acids, for example halocarbonyl, for example chlorocarbonyl, or lower alkanoyloxycarbonyl, for example acetoxycarbonyl. Amidated carboxy contains as the amino group, for example, a free or mono- or di-substituted amino group. Unsubstituted carbamoyl is derived from ammonia and mono- or di-substituted carbamoyl is derived from primary or secondary amine, respectively. Suitable examples of corresponding amidated carboxy are, for example, carbamoyl, carbamoyl mono-substituted by optionally substituted phenyl, carbamoyl mono- or di-substituted by lower alkyl or carbamoyl di-substituted by 4- to 7-membered alkylene or 4- to 7-membered oxa-, aza-, N-lower alkylaza- or thiaalkylene, such as lower alkyleneaminocarbonyl, morpholino- or thiomorpholino-carbonyl, or carbamoyl mono- or di-substituted by lower alkyl optionally containing aryl, such as N-mono- or N-di-lower alkylcarbamoyl. Orthoester groupings are, for example, trialkoxymethyl groupings, such as tri-lower alkoxymethyl groups. Corresponding orthoanhydride groupings are, for example, tri-halomethyl compounds.

Functionally modified hydroxy $X_2$ or $X_4$ should be understood as meaning, for example, functionally modified hydroxy containing an oxy group, such as esterified hydroxy or etherified hydroxy. Esterified hydroxy is, for example, hydroxy esterified by an organic carboxylic acid, such as lower alkanecarboxylic acid, and represents, for example, lower alkanoyloxy, for example acetoxy. Etherified hydroxy is, for example, alkoxy, such as lower alkoxy, for example methoxy or ethoxy. $X_4$ also represents hydroxy esterified by a mineral acid, such as hydrohalic acid, or by a sulphonic acid, such as lower alkane- or optionally substituted benzene-sulphonic acid, for example halogen, methane- or p-toluene-sulphonyloxy.

The cyclisation of compounds of the formula (II) is carried out in customary manner, especially in the manner known from the literature for analogous reactions. Thus, the operation is carried out if necessary in the presence of a catalytic agent, such as an acidic agent. Suitable as acidic agents are, for example, strong inorganic or organic protonic acids, such as mineral acids, for example hydrohalic acids, sulphuric acid or polyphosphoric acid, sulphonic acids, such as alkane- or optionally substituted benzene-sulphonic acids, for example methane- or p-toluene-sulphonic acids, or organic carboxylic acids, such as lower alkanecarboxylic acids, for example glacial acetic acid. It is also possible to use Lewis acids for the cyclisation of compounds of the formula (II), especially for the cyclisation of compounds of the formula (II) in which $X_1$ represents hydrogen and $X_2$ represents a group of the formula —O—CO—CH($R_1$)—$X_4$. There are used as Lewis acids, i.e. electron-acceptors, for example compounds of elements of the third and fifth main groups and also of the second and eighth sub-groups of the Periodic Table. There come into consideration especially halides of boron, aluminium, tin, antimony and iron, for example boron trifluoride, aluminium chloride, tin(IV) chloride, zinc chloride and iron(III) chloride, and also lower alkanoates of thallium, such as thallium(III) acetate. The cyclisation of compounds of the formula (II) is carried out under inert conditions, such as under inert gas, for example nitrogen or argon, in the presence or absence of an inert solvent and/or under pressure, for example in a closed apparatus, and at a suitable reaction temperature, for example at from approximately 0° to approximately 250° C. Solvents are, for example, those that bind the water formed during the reaction, such as anhydrides, for example acetic anhydride, or with the aid of which the water can be removed from the reaction mixture, for example by azeotropic distillation, such as with the aid of aromatic hydrocarbons, for example toluene, benzene or xylenes, also non-polar solvents, such as ether, for example dioxane, halogenated alkanes, for example methylene chloride or chloroform.

In a preferred embodiment of the cyclisation, compounds of the formula (II) are used in which $X_1$ represents a group of the formula —CH($R_1$)—$X_3$ in which $X_3$ is carboxy, and $X_2$ represents hydroxy. In this case it is sufficient to use catalytically active acids in traces. If the operation is carried out in the absence of corresponding protonic acids, the water being formed during the reaction is advantageously removed from the reaction mixture, for example by azeotropic distillation, or bound by suitable water-binding agents, such as alkanecarboxylic acid anhydrides, for example acetic anhydride, or by substituted diimides, such as dicycloalkyl carbodiimides, for example dicyclohexyl carbodiimide.

In a further preferred embodiment, compounds of the formula (II) in which $X_1$ represents a group of the formula —CH($R_1$)—$X_3$ and $X_3$ represents carboxy or esterified or amidated carboxy and $X_2$ represents hydroxy etherified by an alkanol are cyclised by heating with hydriodic acid or hydrobromic acid and optionally a heating with hydriodic acid or hydrobromic acid and a lower alkanecarboxylic acid anhydride, especially acetic anhydride, directly and without isolating intermediates, to form the corresponding compounds of the formula (I).

The starting materials of the formula (II) or their salts can be obtained according to processes known per se. For example, compounds of the formula (IIa)

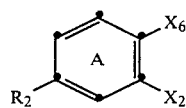

(IIa)

or salts thereof, in which $X_6$ represents a group of the formula $R_1$—$CH_2$—CO—, are used as starting materials and are reacted with ammonium polysulphide under pressure or with sulphur and a primary or secondary amine, advantageously with morpholine or thiomorpholine. In a resulting compound of the formula (II) in which $X_1$ represents a group of the formula —CH($R_1$)—$X_3$, $R_1$ represents hydrogen and $X_3$ represents correspondingly substituted thiocarbamoyl or carbamoyl, or ammonium carboxylate, $X_3$ is converted by solvolysis, for example by hydrolysis, into carboxy, or especially by alcoholysis into a correspondingly esterified carboxy group $X_3$.

In an optional additional reaction, compounds of the formula (IIa) in which $X_6$ is a group of the formula $R_1$—$CH_2$—CO— and $R_1$ is hydrogen can be converted into compounds of the formula (IIa) in which $X_6$ is a group of the formula $R_1$—$CH_2$—CO— and $R_1$ represents an aliphatic radical. This is generally carried out by treatment with a reactive esterified aliphatic alcohol, such as a lower alkyl halide, in the presence of a strong base, such as an alkali metal alcoholate, for example sodium methoxide. Compounds of the formula (II) in which $X_2$ represents reactive esterified hydroxy and $X_1$ is a group of the formula —CH($R_1$)—$X_3$ and $X_3$, for example, represents functionally modified carboxy are advantageously reacted under hydrolytic conditions in situ without isolation to form corresponding compounds of the formula (I). In compounds of the formula (II) in which $X_2$ represents etherified hydroxy, the ether grouping is advantageously cleaved, for example by treatment with a strong acid, such as a hydrohalic acid, for example hydriodic acid, or with pyridine hydrochloride.

In a further, especially preferred embodiment of the cyclisation process, compounds of the formula (Ia) in which $R_1$ represents methyl and $R_a$, $R_b$ and $R_c$ each represents hydrogen or lower alkyl, or $R_a$ and $R_b$ together represent 3- or 4-membered alkylene and $R_c$ has the meaning given above, are obtained by reacting compounds of the formula

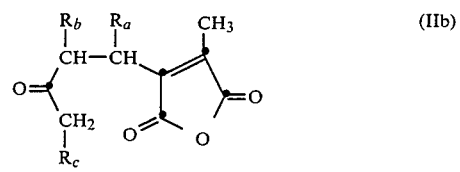

(IIb)

which are known or can be manufactured as described below, with amines of the formula $R_2$—H (IIc) or their acid addition salts. In this case, compounds of the formula (II) in which $X_1$ represents a group of the formula —CH($CH_3$)—COOH and $X_2$ represents hydroxy may be formed for example intermediately and cyclise directly under the reaction conditions to form the corresponding compounds of the formula (Ia).

The reaction is carried out, for example, at elevated temperature, for example in the melt or at the reflux temperature of the solvent, for example in a temperature range of from approximately 80° C. to approximately 200° C. Suitable inert solvents are, for example, higher-boiling hydrocarbons, such as aromatic hydrocarbons, for example benzene, toluene or xylenes. The amines of the formula (IIc) are used especially in the form of acid addition salts, for example advantageously as benzoates.

For the manufacture of compounds of the formula (IIb) in which $R_a$ represents hyrogen, compounds of the formula

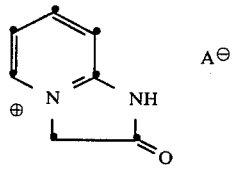
(IId)

that are optionally substituted in the aromatic moiety and in which $A^\ominus$ represents the anion of an inorganic or organic acid are used as starting materials and are reacted with fumaric acid, maleic acid or maleic acid anhydride in the presence of a base, inorganic or organic bases being suitable. Inorganic bases are, for example, alkali metal hydroxides or hydrides, such as sodium or potassium hydroxide or sodium or potassium hydride. There are used as organic amines, for example, tertiary amines, such as trialkylamines, for example triethylamines or tri-n-butylamines, or cyclic amines, such as pyridine, picoline, quinoline or lutidine.

The free compounds initially obtainable by this method are converted by treatment with organic or inorganic acids into the compounds of the formula

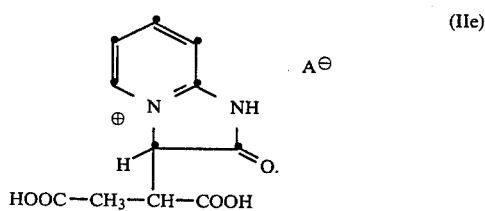
(IIe)

In the further course of the reaction, these compounds are reacted, optionally in the presence of one of the above-mentioned bases, with compounds of the formula $R_a$—CH=C($R_b$)—CO—CH$_2$—$R_c$ (IIf) to form compounds of the formula

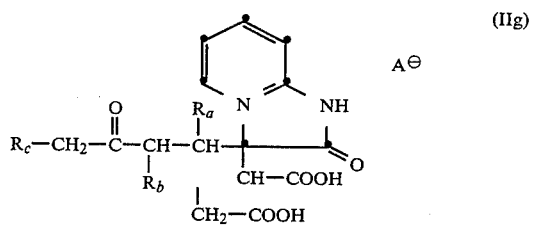
(IIg)

which are converted in the next reaction step by heating, for example at temperatures of between 80° and 160° C., with decarboxylation, into compounds of the formula

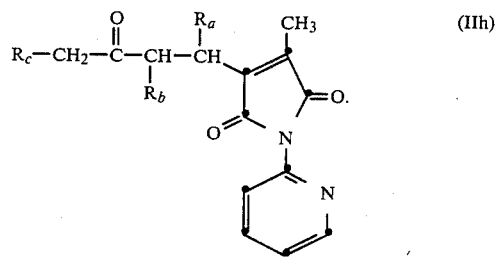
(IIh)

The thermal conversion of compounds of the formula (IIg) into compounds of the formula (IIh) is carried out, for example, in an optionally halogenated aromatic solvent, such as benzene, toluene, a xylene or chlorobenzene or a lower alkanecarboxylic acid, such as glacial acetic acid. The compounds of the formula (IIh) are then hydrolysed to form compounds of the formula (IIb). The hydrolysis is carried out, for example, in aqueous or aqueous-organic medium. Suitable organic solvents are especially high-boiling polar solvents, such as ether, for example dioxane or tetrahydrofuran, N,N-dialkylamides, for example N,N-dimethylformamide or N,N-dimethylacetamide, or cyclic amides, such as N-methylpyrrolidone. The hydrolysis is carried out, for example, with the aid of an inorganic or organic acid, mineral acids, such as hydrohalic acids or sulphuric acid, being suitable as inorganic acids, and sulphonic acids, such as lower alkane- or optionally substituted benzene-sulphonic acids, such as methane- or p-toluene-sulphonic acid, or optionally substituted alkanecarboxylic acids, such as glacial acetic acid, being suitable as organic acids.

For the manufacture of compounds of formula (IIb) in which $R_a$ is other than hydrogen, compounds of the formula (IId) are used as starting materials and are reacted first with compounds of the formula (IIf) and then with fumaric acid, maleic acid or especially with maleic acid anhydride to form compounds of the formula (IIg) which, in turn, as described above, further react to form the corresponding compounds of the formula (IIb).

Re variant (b):

The starting materials of the formula (III) can be used in the form of salts, especially acid addition salts.

A group Y that can be converted into the group of the formula >CH($R_1$) can be converted, for example by reduction, into the group >CH($R_1$).

A compound of the formula III contains, for example, as the group Y that can be converted into >CH($R_1$), a group of the formula >C($R_1$)—COOH.

Such compounds are decarboxylated according to methods known per se to form compounds of the formula (I). The decarboxylation is generally carried out at elevated temperature, for example in a temperature range of approximately from 80° to 250° C., optionally in the presence of a catalytically active agent, for example a noble metal, such as copper powder, or an amine, such as an aromatic amine, for example aniline or quinoline, and optionally in an inert solvent. Suitable inert solvents are, for example, high-boiling optionally halogenated hydrocarbons, such as halogenated aromatic compounds, for example chlorobenzene or a xylene.

For the manufacture of starting materials of the formula (III) in which Y represents a group of the formula >C($R_1$)—COOH, compounds of the formula

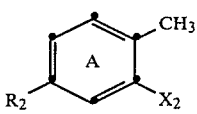

in which $X_2$ represents hydroxy or functionally modified hydroxy, or salts thereof, are used as starting materials and the methyl group is halogenated. For this purpose there is used, for example, N-halosuccinimide, such as the corresponding bromo- or chloro-derivative, sulphuryl chloride, bromine or chlorine, and the operation is preferably carried out in the presence of a radical-former, such as a peroxide, for example benzoyl peroxide, or an azo compound, for example azobisisobutyronitrile, or by the introduction of energy, such as irradiation, for example with UV light. The corresponding halogen is then exchanged for a cyano group by reaction with an alkali metal cyanide, such as sodium or potassium cyanide. The resulting acetonitrile is reacted with a dialkyl carbonate, such as diethyl carbonate, in the presence of an alkali metal, such as sodium, to form a compound of the formula

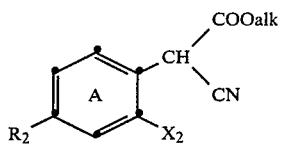

in which alk represents an alkyl radical. In the next reaction step, it is possible, if desired, to introduce the radical $R_1$ by treatment with a corresponding halide or tosylate in the presence of a strong base, such as an alkali metal alkoxide, for example sodium methoxide, potassium methoxide or potassium tert.-butoxide, or an alkali metal amide or hydride, for example sodium amide or potassium hydride. The subsequent hydrolysis results in compounds of the formula

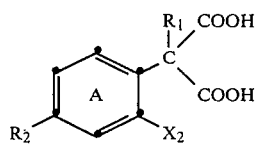

which are cyclised in the presence of an acid, for example a protonic acid, such as a mineral acid, for example hydrohalic acid or sulphuric acid, such as alkane- or optionally substituted benzene-sulphonic acid, for example p-toluenesulphonic acid, or such as lower alkanecarboxylic acid, for example acetic acid, or a Lewis acid, such as a halide of elements of the third and fifth main groups and also the second and eighth sub-groups of the Periodic Table, for example aluminium(III) chloride or iron(III) chloride, to form corresponding compounds of the formula (III).

In a further preferred embodiment, it is possible to obtain compounds of the formula (III) in which Y represents the group $>C(R_1)$—COOH by using as starting material a compound of the formula (IIa) or a salt thereof in which $X_6$ represents a group of the formula $R_1$—$CH_2$—CO— and reacting this compound with ammonium polysulphide under pressure or with sulphur and a primary or secondary amine, advantageously with morpholine or thiomorpholine. In a resulting compound of the formula (II) in which $X_1$ represents a group of the formula —$CH(R_1)$—$X_3$, $R_1$ represents hydrogen and $X_3$ represents correspondingly substituted thiocarbamoyl or carbamoyl, or ammonium carboxylate, $X_3$ is converted by solvolysis, for example by hydrolysis, into carboxy.

In an optional additional reaction, compounds of the formula (IIa) in which $R_1$ is hydrogen can be converted into compounds of the formula (IIa) in which $R_1$ represents an aliphatic radical. This is generally carried out by treatment with a reactive esterified aliphatic alcohol, such as a lower alkyl halide, in the presence of a strong base, such as an alkali metal alcoholate, for example sodium methoxide. In compounds of the formula (II) in which $X_2$ represents etherified hydroxy, the ether grouping is advantageously cleaved, for example by treatment with a strong acid, such as a hydrohalic acid, for example hydriodic acid, or with pyridine hydrochloride.

The resulting compounds of the formula

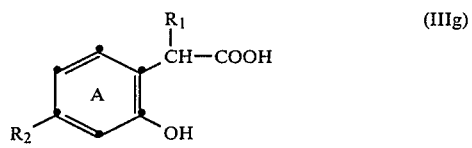

are treated with pivalic acid chloromethyl ester in the presence of potassium iodide in dimethylformamide/acetone. From this there results a corresponding compound of the formula (III) in which Y represents a group of the formula $>C(R_1)$—$CH_2OH$. The hydroxymethyl group can then be oxidised in the normal manner to form carboxy, for example with a basic potassium permanganate solution.

The group Y can also represent a group of the formula $>C=R'_1$ in which $R'_1$ represents a divalent aliphatic radical, for example alkylidene, especially lower alkylidene, a tautomeric form thereof, such as alkenylene, or alkenylidene, such as lower alkenylidene. Corresponding compounds of the formula (III) can be converted by reduction into compounds of the formula (I). The reduction can be carried out by catalytic hydrogenation with hydrogen, for example under a protective gas, such as nitrogen, and in the presence of a suitable hydrogenation catalyst, or by reaction with optionally complex hydrides, such as borane in tetrahydrofuran, or such as alkali metal borohydrides together with halides of elements of the third main group, for example with sodium borohydride and aluminium chloride or boron trifluoride in diglyme. Suitable hydrogenation catalysts are, for example, elements of the eighth sub-group or derivatives thereof, such as oxides or carbonates, which are optionally supported on a carrier, such as alkaline earth metal carbonates, for example barium carbonate, or active carbon. Examples of such catalysts are Raney-nickel, platinum oxide or palladium-on-carbon. Inert solvents are, for example, ethers, such as dioxane or tetrahydrofuran, or alkohols, such as lower alkanoles. The hydrogenation is for example carried out in a temperature range of from approximately −80° to approximately 200° C.

For the manufacture of starting materials of the formula (III) in which Y represents a group of the formula $>C=R'_1$, the procedure is according to methods known per se. Thus, for example, compounds of the formula (IIIc) are halogenated in the side chain $R_1$, for example using chlorine or bromine, N-chlorosuccinimide or N-bromosuccinimide, optionally in the presence of a radical-former, such as benzoyl peroxide or azobisisobutyronitrile. A $CO_2$ equivalent is then removed in customary manner by decarboxylation. In the next reaction step, dehydrohalogenation is carried out in the presence of a base, such as an alkali metal alkoxide, for example potassium tert.-butoxide, to form the corresponding compounds of the formula

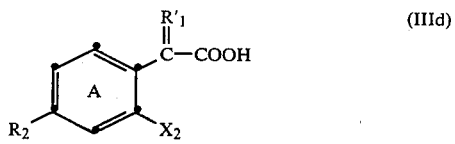   (IIId)

in which $X_2$ represents hydroxy or functionally modified hydroxy and which are cyclised, for example in the presence of an acid, for example a strong protonic or Lewis acid. Protonic acids are, for example, mineral acids, such as hydrohalic acids or sulphuric acid, alkane- or optionally substituted benzene-sulphonic acids, for example p-toluenesulphonic acid, or alkanecarboxylic acids, such as glacial acetic acid. Suitable as Lewis acids are, for example, halides of boron, aluminium, tin, antimony or iron, such as boron trifluoride or aluminium chloride. The cyclisation is preferably carried out with hydriodic or hydrobromic acid and acetic anhydride or, if $X_2$ represents hydroxy, with a carbodiimide, such as dicyclohexyl carbodiimide.

Furthermore, for example, those groups Y in which Y represents a group of the formula $>C(R_1)-X_{11}$ and $X_{11}$ represents hydroxy, alkylthio, dialkylamino or diphenylsulphamoyl each phenyl moiety of which may optionally be substituted, or in which Y represents carbonyl, can be converted by reduction into the group $>CH(R_1)$.

Alkylthio $X_{11}$ is, for example, lower alkylthio, especially methyl- or ethyl-thio, and dialkylamino $X_{11}$ is, for example, di-lower alkylamino, especially dimethylamino. Each phenyl moiety of diphenylsulphamoyl may optionally be substituted by, for example, halogen or lower alkyl, and diphenylsulphamoyl may especially be di-(p-bromophenyl)- or di-(p-toluene)sulphamoyl.

The reduction is carried out in a manner known per se. Thus, a suitable reducing agent is used and the operation is carried out under inert conditions, such as optionally under a protective gas, such as nitrogen, in an inert solvent or diluent, if necessary under pressure and/or while cooling or heating. Solvents are for example ethers, such as dioxane or tetrahydrofuran, or alkoholes, such as lower alkanoles. The reaction is carried out for example in a temperature range of from approximately $-80°$ to approximately 250°.

There is used as reducing agent, for example, elemental hydrogen which is activated by a hydrogenation catalyst, also an optionally complex hydride or red phosphorus in the presence of hydrogen iodide or iodine. Suitable hydrogenation catalysts are elements of sub-group VIII of the Periodic Table or a derivative, for example a corresponding oxide, thereof. Such catalysts may be supported on a carrier, for example on active carbon, an alkaline earth metal carbonate or sulphate and also on a silica gel. Examples of such hydrogenation catalysts are, for example, platinum, platinum oxide or palladium, which are optionally supported on active carbon or barium sulphate, or Raney-nickel. Suitable as optionally complex hydrides are, for example, hydrides of elements of the first to third main groups or complex hydrides formed therefrom, such as diborane, aluminium hydride, lithium or sodium borohydride, lithium or sodium aluminium hydride, and also other complex hydrides, such as lithium triethyl borohydride.

In a preferred embodiment of the process, hydroxy, alkylthio, such as lower alkylthio, especially methylthio, and also dialkylamino, such as di-lower alkylamino, especially dimethylamino, are reduced by catalytically activated elemental hydrogen, palladium-on-carbon or Raney-nickel, for example, being used as the hydrogenation catalyst. The hydroxy group can also be replaced by hydrogen by using red phosphorus in the presence of hydriodic acid or iodine while heating, for example at from approximately 100° to approximately 250° C. In a further preferred method, the diphenylsulphamoyl group, each phenyl moiety of which may optionally be substituted, is reduced using a suitable optionally complex hydride, for example using an alkali metal borohydride, while heating, for example at from approximately 100° to approximately 200° C.

The carbonyl group Y is preferably reduced by a hydrazine in the presence of a base, such as an alkali metal hydroxide, analogously to the Wolff-Kishner reduction, or the Huang-Minlon-variante respectively, or by a selective complex hydride, such as sodium cyanoborohydride in the presence of p-toluene-sulphonyl hydrazide, to form the group $>CH(R_1)$ in which $R_1$ represents hydrogen.

The starting compounds of the formula (III) in which Y represents the group of the formula $>C(R_1)-OH$ can be obtained, for example, by reacting a compound of the formula

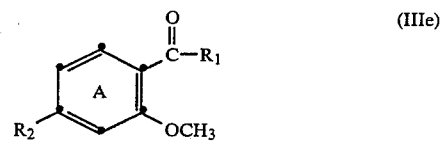   (IIIe)

with hydrocyanic acid to form the corresponding cyanohydrin. After hydrolysing the cyano group and cleaving ether, cyclisation is carried out, preferably in situ, in the presence of an acid or a dehydration agent to form the corresponding compound of the formula III.

Starting compounds of the formula (III) in which Y represents the group of the formula $>C(R_1)-X_{11}$ and $X_{11}$ represents alkylthio and $R_1$ is hydrogen can be obtained by using a compound of the formula (IIIe) as starting material and treating it with a trihalomethane, such as chloroform, in the presence of a base, introducing the alkylthio group by reaction with an alkanethiol, then cleaving the ether with a suitable acid, for example a strong hydrohalic acid, and hydrolysing the trihalomethyl group with a base, such as an alkali metal hydroxide, to form the carboxy group. In the last step, the cylisation catalysed by an acid, such as protonic acid, takes place to form the corresponding compound of the formula (III). In an optional further step compounds of the formula (I) in which $R_1$ is hydrogen can be converted into compounds of the formula (I) in which $R_1$ denotes an aliphatic radical. This can be effected by treating with a reactive esterified aliphatic alkohol, such as a lower alkylhalide, in the presence of a strong base, such as an alkalimetal alkoholate, for example sodium methylate.

Likewise using a compound of the formula (IIIe) as starting material, it is possible to obtain compounds of the formula (III) in which Y represents the group >C(R₁)—X₁₁ and X₁₁ represents dialkylamino or diphenylsulphamoyl, each phenyl moiety of which may optionally be substituted. For this purpose, for example, a compound of the formula (IIIe) can be reacted with sodium cyanide and ammonium carbonate to form the hydantoin obtainable in this manner which can be hydrolysed using a base, such as an alkali metal hydroxide, to form the corresponding amino acid. The free amino group is then converted into the desired group $X_{11}$ for example by alkylation using an alkyl halide or by acylation using the corresponding sulphonyl halide. By simultaneously cleaving ether and cyclising, for example with hydrobromic acid and acetic anhydride, the desired starting compounds of the formula (III) can finally be obtained.

The starting material of the formula (III) in which Y represents carbonyl can be obtained, for example, by reacting a compound of the formula

(IIIf)

with oxalyl chloride under cyclising conditions, such as in the presence of a strong acid.

Re variant (c):

The starting materials of the formula (IV) can be used in the form of their salts, especially acid addition salts.

A radical $X_5$ that can be converted into $R_2$ represents, for example, a group of the formula —NH—A₁—X₇, in which A₁ represents a divalent hydrocarbon, such as optionally branched lower alkylene, and $X_7$ represents hydrogen, 3- to 7-membered cycloalkyl, or aryl, such as, for example, phenyl that is unsubstituted or substituted by an aliphatic radical, lower alkoxy, lower alkanethio, lower alkansulphinyl, lower alkanesulphonyl, hydroxy, halogen, lower alkanoyloxy, lower alkanoyl and/or nitro.

The conversion of —NH—A₁—X₇ into R₂ is carried out in a manner known per se. Thus, for example, a compound of the formula (IV) or a salt thereof is reacted with a compound of the formula X₇—A₁—X₈ (IVa) in which X₈ represents optionally reactive esterified hydroxy. Reactive esterified hydroxy X₈ is, for example, hydroxy esterified by a strong inorganic mineral acid, such as hydrohalic acid or sulphuric acid, by an organic sulphonic acid, such as lower alkane- or optionally substituted benzene-sulphonic acid, for example methane- or p-toluene-sulphonic acid, or by an organic carboxylic acid, such as lower alkanecarboxylic acid, for example acetic acid. The operation is carried out, for example, if necessary in the presence of a base, such as an alkali metal alkanol, an alkali metal or alkaline earth metal hydroxide or carbonate, for example sodium methoxide, sodium hydroxide or sodium bicarbonate, under inert conditions, such as under a protective gas, for example nitrogen, and/or in the presence or absence of an inert solvent in a temperature range of from approximately 0° to approximately 150° C. A solvent is for example an ether, such as dioxane, a ketone, such as acetone, a carboxylic acid, such as glacial acetic acid, or an amide, such as dimethylformamide.

For the manufacture of starting materials of the formula (IV) the starting material used is, for example, a compound of the formula

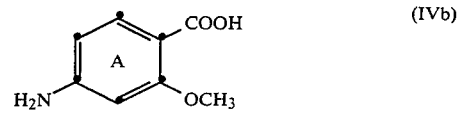

(IVb)

or a salt thereof, which is reacted, for example, with a benzyl halide, such as benzyl chloride, in the presence of a base, such as an alkali metal hydroxide, for example sodium hydroxide, and then with dilute acid. The resulting 4-N,N-dibenzylamino-2-methoxybenzoic acid is converted into the corresponding acid chloride using thionyl chloride. In the next reaction step, reaction is carried out with diazomethane, to obtain a compound of the formula

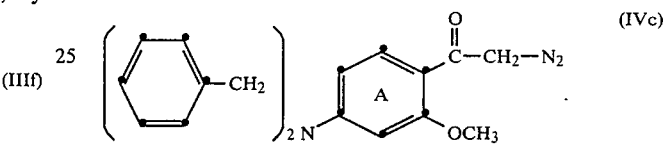

(IVc)

The compound of the formula (IVc) is then solvolysed in the presence of silver or silver oxide or with simultaneous UV irradiation, hydrolysis resulting in the compound of the formula

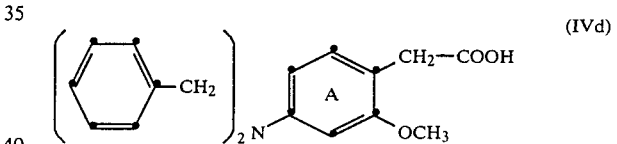

(IVd)

or its salt and alcoholysis resulting in the corresponding ester of the compound (IVd).

If desired, the radical R₁, R₁ being other than hydrogen, can be introduced into compounds of the formula (IVd), for example by treatment with a reactive esterified aliphatic alcohol, for example with a hydrohalic acid. The two benzyl groups are then removed, for example by catalytic hydrogenation. The resulting reaction product is cyclised, for example using 48% hydrobromic acid and acetic anhydride, to form the compound of the formula

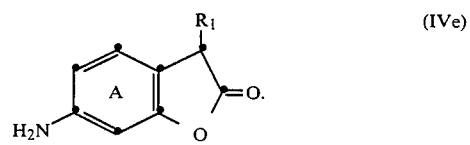

(IVe)

By reaction with a compound of the formula X₇—A₁—X₈ in the presence of a base, the amino group can be converted into the group X₅.

Compounds of the formula (I) in which R₂ represents N,N-di-lower alkylamino can also be obtained by treating compounds of the formula (IV) in which X₅ represents amino with di-lower alkyl sulphates, for example dimethyl sulphate, or analogous to the Leukart-Wallach reaction with carbonyl compounds, such as aldehydes or ketones, and formic acid.

Likewise, amines $R_2$—H, sufficiently nucleophile, can be introduced directly into compounds of the formula (IV), in which $X_5$ denotes a radical replaceable by the radical $R_2$. In case $X_5$ denotes for example halogen, preferable chlorine, bromine or iodine, the reaction can be carried out in the presence or absence of a solvent and, according to the choice of halogen, at low temperature up to the boiling point of the corresponding solvent. Preferably, in the position adjacent to $X_5$, a substituent is located having a strong —I— or —M—effect, such as nitro, halogen or trifluoromethyl. Sometimes it will be advantageous carrying out the reaction under pressure or at elevated temperature. Preferably, the amines are used in excess. In case, compounds of the formula (IV), in which $X_5$ is hydrogen are used, they are first of all treated with an oxidizing agent, such as lead tetracetate, for example in presence of a suitable acid, such as glacial acetic acid, and at room temperature and are subsequently reacted with the corresponding amine $R_2$—H in an inert solvent, such as an ether, for example dioxane, under warming, for example at the refluxing temperature of the corresponding solvent.

Re variant (d):

The starting materials of the formula (V) can be used in the form of their salts, especially in the form of acid addition salts.

A group Z that can be converted into the carbonyl group is, for example, the methylene group or represents a radical that can be hydrolysed to form the carbonyl group.

The methylene group can be converted into the carbonyl group, for example by oxidation. The oxidation is carried out in a manner known per se, for example using a suitable oxidising agent, under inert conditions, for example in an inert solvent or diluent and while cooling or heating.

Suitable as oxidising agents are, for example, oxides of elements of the sub-group VIII of the Periodic Table, such as osmium tetroxide or, especially, ruthenium tetroxide, and also hypochlorites, such as alkali metal or alkaline earth metal hypochlorites, for example sodium or calcium hypochlorite. A solvent is, for example, water, an alkohole, such as a lower alkanole, a ketone, such as acetone, an ether, such as dioxane or tetrahydrofuran, an amide, such as dimethylformamide, or a mixture thereof.

Suitable as groups that can be converted by hydrolysis into the carbonyl group are, for example, thiocarbonyl or optionally N-substituted iminomethylene. As substituents of imino there may be mentioned, for example, an optionally substituted hydrocarbon radical, such as an aliphatic or aromatic radical, for example lower alkyl or optionally substituted phenyl, or an acyl group derived from a carboxylic acid or a semiester of carbonic acid, such as lower alkanoyl or optionally substituted benzoyl, or optionally substituted alkoxycarbonyl, such as lower alkoxycarbonyl.

The hydrolysis is carried out, for example, in the presence or absence of a solvent or diluent, if necessary while cooling or heating and/or under inert gas, for example nitrogen. A solvent is, for example, water, an alkhohole, such as a lower alkanole, a ketone, such as acetone, an ether, such as dioxane or tetrahydrofuran, an amide, such as dimethylformamide, or a mixture thereof.

The starting material of the formula (V) in which Z represents methylene can be obtained, for example, by etherifying a compound of the formula

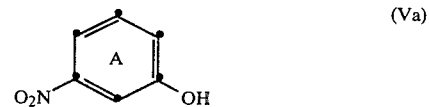

with a compound of the formula $R_1$—CO—$CH_2$—Cl (Vb) and cyclising this ether with titanium(III) chloride in a lower alkanol to form the compound of the formula

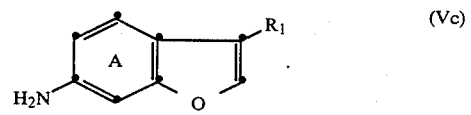

After converting the free amino group into $R_2$, for example by customary alkylation, the double bond of the benzofuran in question is hydrogenated by reduction, for example using an optionally complex hydride, especially using potassium borohydride, to form the corresponding compound of the formula (V).

The starting material of the formula (V) in which Z represents thiocarbonyl can be obtained, for example, by using as starting materials, for example, compounds of the formula (IIa) or salts thereof in which $X_6$ represents a group of the formula $R_1$—$CH_2$—CO— and reacting these with ammonium polysulphide under pressure or with sulphur and a primary or secondary amine, advantageously with morpholine or thiomorpholine. In a resulting compound of the formula (II) in which $X_1$ represents a group of the formula —CH($R_1$)—$X_3$, $R_1$ represents hydrogen and $X_3$ represents correspondingly substituted thiocarbamoyl or carbamoyl, or ammonium carboxylate, $X_3$ is converted by solvolysis, for example by hydrolysis, into carboxy.

In an optional additional reaction, compounds of the formula (IIa) in which $X_6$ is a group of the formula $R_1$—$CH_2$—CO and $R_1$ is hydrogen can be converted into compounds of the formula (IIa) in which $X_6$ is a group of the formula $R_1$—$CH_2$—CO and $R_1$ represents an aliphatic radical. This is generally carried out by treatment with a reactive esterified aliphatic alcohol, such as a lower alkyl halide, in the presence of a strong base, such as an alkali metal alcoholate, for example sodium methoxide.

In resulting compounds of the formula (II) in which $X_2$ represents etherified hydroxy, the ether grouping is advantageously cleaved, for example by treatment with a strong acid, such as a hydrohalic acid, for example hydriodic acid, or with pyridine hydrochloride. In resulting compounds of the formula (IIIg), the carboxy group are converted into the dithiocarboxy group, for example via an ester with a thiol with subsequent treatment with phosphorus pentasulphide. In the last step, cyclisation can be carried out to form the corresponding compound of the formula (V).

Re variant (e):

The starting compounds of the formula (VI) may be in the form of their salts, especially in the form of acid addition salts.

A ring A' that can be converted into the ring A contains, for example, the substitution pattern of the ring A and two double bonds and, in addition, at two carbon atoms, one hydrogen atom in each case. Accordingly, conversion into the ring A can be carried out by dehydrogenation.

Dehydrogenation is carried out in a manner known per se. A suitable dehydrogenation agent is used and the operation is carried out, if necessary, while heating, for example in a temperature range of from approximately 100° to approximately 300° C., in an inert solvent or diluent, optionally under a protective gas, such as nitrogen, and/or, if necessary, under pressure.

There come into consideration as dehydrogenation agents, for example, elements of the sub-groups, preferably those of the sub-group VIII of the Periodic Table, such as palladium or platinum, or corresponding salts, such as ruthenium triphenyl phosphide chloride; the agents may be supported on suitable carriers, such as active carbon, aluminium oxide or a silica. Further preferred dehydrogenation agents are, for example, quinones, such as p-benzoquinones, for example tetrachloro-p-benzoquinone or 2,3-dichloro-5,6-dicyano-p-benzoquinone, or such as anthraquinones, for example phenanthrene-9,10-quinone. It is also possible to use N-halosuccinimides, such as N-chlorosuccinimide, manganese compounds, such as barium manganate or manganese dioxide, and selenium derivatives, such as selenium dioxide or diphenylselenium bis-trifluoroacetate.

The starting material of the formula (VI) in which $R_1$ represents methyl can be obtained, for example, by using a compound of the formula (IIb) as the starting material and reacting it with an acid addition salt of a compound of the formula $R_2$—H.

A compound of the formula (I) obtainable according to the invention can be converted in a manner known per se into a different compound of the formula (I).

A hydrogen atom as substituent of an aromatic ring system can be replaced in a manner known per se in the presence of a halogenating agent by a halogen atom.

For example the replacement of hydrogen by bromine can be effected for example by elementory bromine according to "Methoden der Organischen Chemie", Houben-Weyl, Vol. 5/4, pp. 233–249, in an inert solvent. Furthermore, the bromation can be effected by the following bromating agents: hypobromous acid, acylhypobromides or further organic bromide compounds, for example N-bromosuccinimide, N-bromoacetamide, N-bromophthalimide, pyridinium perbromide, dioxane, dibromide, 1,3-dibromo-5,5-dimethyl-hydantoin and 2,4,4,6-tetrabromo-2,5-cyclohexadien-1-one.

The corresponding chlorination can be effected according to Houben-Weyl (4. Edition), Vol. 5/3, pp. 651–673, for example, preferably with elementory chlorine, for example in a halogenated hydrocarbon, such as chloroform, and under cooling, for example at approximately —10° to approximately +10° C.

The replacement of hydrogen by iodine can be effected by elementory iodine in the presence of mercury oxide or nitric acid. Instead of using elementory iodine, it is possible to use for example also potassium iodine in the presence of a thallium salt, for example thallium (III)-trifluoracetate according to tetrahedron Lettres (1969), p. 2427.

It is also possible to alkylate the benzo moiety of the ring system, for example with a lower alkanol or a lower alkyl halide or a phosphoric acid lower alkyl ester in the presence of Lewis acids (Friedel-Crafts-alkylation). In a compound of the formula (I) in which the aromatic ring A contains bromine, it is possible, for example, to replace the bromine by lower alkyl by reaction with a lower alkyl bromide in the presence of an alkali metal.

A hydrogen atom in an aromatic ring can be replaced by an acyl group in an manner known per se. For example, the introduction of the acyl group can be effected analogous to the Friedel-Crafts-acylation (cf. G. A. Olah, Friedel-Crafts and Related Reactions, Vol. I, Interscience, New York, 1963–1965), for example by reaction with a reactive functional derivative, especilly a halide or an anhydride, of an organic carboxylic acid in the presence of a Lewis acid, for example aluminium chloride, antimony(III)-chloride or antimony(V)-boron chloride, iron(III)-chloride, zinc(II)-chloride trifluoride If the aromatic ring A contains hydroxy as substituent, then the hydroxy can be etherified in a manner known per se. The reaction with an alcohol component, for example with a lower alkanol, such as ethanol, in the presence of acids, for example mineral acid, such as sulphuric acid, or in the presence of dehydrating agents, such as dicyclohexyl carbodiimide, results in lower alkoxy. Conversely, ethers can be cleaved into phenols by treatment with acids, such as mineral acids, for example hydrohalic acid, such as hydrobromic acid, or such as Lewis acids, for example halides of elements of the third main group, such as boron tribromide, or by treatment with pyridine hydrochloride or thiophenol.

Furthermore, hydroxy can be converted into lower alkanoyloxy, for example by reaction with a desired lower alkanecarboxylic acid, such as acetic acid, or a reactive derivative thereof, for example in the presence of an acid, such as a protonic acid, for example hydrochloric acid, hydrobromic acid, sulphuric acid, phosphoric acid, or a benzenesulphonic acid, in the presence of a Lewis acid, for example boron trifluoride etherate, or in the presence of a water-binding agent, such as dicyclohexyl carbodiimide. Conversely, esterified hydroxy can be solvolysed, for example by base catalysis, to form hydroxy.

If the ring A is substituted by lower alkylthio, the latter can be oxidised in customary manner to form the corresponding lower alkane-sulphinyl or -sulphonyl. There come into consideration as suitable oxidising agents for the oxidation to the sulphoxide stage, for example, inorganic peracids, such as peracids of mineral acids, for example periodic acid or persulphuric acid, organic peracids, such as corresponding percarboxylic or persulphonic acids, for example performic, peracetic, trifluoroperactic or perbenzoic acid or p-toluenepersulphonic acid, or mixtures of hydrogen peroxide and acids, for example a mixture of hydrogen peroxide and acetic acid.

The oxidation is often carried out in the presence of suitable catalysts; there may be mentioned as catalysts suitable acids, such as optionally substituted carboxylic acids, for example acetic acid or trifluoracetic acid, or transition metal oxides, such as oxides of elements of sub-group VII, for example vanadium, molybdenum or tungsten oxide. The oxidation is carried out under mild conditions, for example at temperatures of from approximately —50° to approximately +100° C.

The oxidation to the sulphone stage can also be carried out correspondingly with dinitrogen tetroxide as the catalyst in the presence of oxygen at low temperatures, as can the direct oxidation of the lower alkylthio to form the lower alkanesulphonyl. In this case, however, the oxidising agent is normally used in excess.

If the ring A of the formula I is substituted by lower alkyl-sulphinyl or -sulphonyl, it is possible to reduce this according to methods known per se to form the corresponding lower alkylthio compound, and, when using lower alkanesulphonyl derivatives as starting materials, also to form lower alkanesulphinyl. Suitable as reducing agents are, for example, catalytically activated hydrogen, there being used noble metals or oxides, such as palladium, platinum or rhodium or their oxides, optionally supported on a suitable carrier, such as active carbon or barium sulphate. Also suitable are reducing metal cations, such as tin(II), lead(II), copper(I), manganese(II), titanium(II), vanadium(II), molybdenum(III) or tungsten(III) compounds, hydrogen halides, such as hydrogen chloride, bromide or iodide, hydrides such as complex metal hydrides, for example lithium aluminium hydride, sodium borohydride, tributyltin hydride, phosphorus compounds, such as phosphorus halides, for example phosphorus trichloride, phosphorus tribromide, phosphorus pentachloride or phosphorus oxychloride, phosphines, such as triphenylphosphine, or phosphorus pentasulphide pyridine, or sulphur compounds, such as mercaptans, thio acids, such as thiophosphoric acids or dithiocarboxylic acids, dithionite or sulphur/oxygen complexes, such as an iodine/pyridine/sulphur dioxide complex.

Compounds of the formula (I) containing unsaturated radicals, such as lower alkenyl or lower alkenylen, can be converted in a matter known per se into corresponding compounds containing saturated radicals. For example, the hydrogenation of multiple bonds can be effected by catalytic hydrogenation in the presence of hydrogenating catalysts, which are for example precious metals or a derivative thereof, such us an oxide thereof, such as Nickel, Raney-Nickel, Palladium, Platinum oxide, which agents may be supposed on suitable carriers, such as carbon or calcium carbonate. The hydrogenation can be effected preferably at a pressure between 1 and approximately 100 at. and at temperatures between approximately $-80°$ to approximately $200°$ C., more especially between room temperature and approximately $100°$ C. The reaction is carried out practically in a solvent, such as in water in a lower alkanol, for example ethanol, isopropanol or n-butanol, in an ether, for example dioxane, or in a lower alkanecarboxylic acid, for example acetic acid.

Salts of compounds of the formula (I) can be manufactured in a manner known per se. Thus, for example, acid addition salts of compounds of the formula (I) are obtained by treatment with an acid or a suitable ion exchange reagent. Salts can be converted in customary manner into the free compounds; for example, acid addition salts can be converted by treatment with a suitable basic agent.

As a result of the close relationship between the novel compounds in free form and in the form of their salts, hereinbefore and hereinafter the free compounds or their salts shall be understood to mean optionally also the corresponding salts or free compounds, respectively, where appropriate with regard to meaning and purpose.

The novel compounds, including their salts, can also be obtained in the form of their hydrates, or include other solvents used for the crystallisation.

Depending upon the starting materials and methods chosen, the novel compounds may be in the form of one of the possible isomers or in the form of mixtures thereof, for example, depending on the number of asymmetric carbon atoms, in the form of pure optical isomers, such as antipodes, or in the form of mixtures of isomers, such as racemates, mixtures of diastereoisomers or mixtures of racemates.

Resulting mixtures of diastereoisomers and mixtures of racemates can be separated on the basis of the physico-chemical differences between the constituents, in known manner, into the pure isomers, diastereoisomers or racemates, for example by chromatography and/or fraction crystallisation. Resulting racemates can furthermore be resolved into the optical antipodes by known methods, for example by recrystallisation from an optically active solvent, with the aid of microorganisms or by converting into diastereoisomeric salts or esters, for example by reacting an acidic end product with an optically active base that forms salts with the racemic acid, or with an optically active carboxylic acid or a reactive derivative thereof, and separating the mixture of diastereoisomers obtained in this manner, for example on the basis of their different solubilities, into the diastereoisomers, from which the desired enantiomer can be freed by the action of suitable agents. Advantageously, the more active enantiomer is isolated.

The invention relates also to those embodiments of the process according to which compounds obtainable as intermediates at any stage of the process are used as starting materials and the remaining steps are carried out or a starting material is used in the form of a salt or, especially, is formed under the reaction conditions.

In the process of the present invention it is preferable to use those starting materials which result in the compounds described at the beginning as being especially valuable. The invention relates also to novel starting materials, their use, for example as the active ingredients of medicaments, to formulation processes and to processes for their manufacture.

The pharmaceutical preparations according to the invention, which contain the compound according to the invention or pharmaceutically acceptable salts thereof, are for optical application, and also for enteral, such as oral or rectal, and parenteral administration to (a) warm-blooded animal(s) and contain the pharmacological active ingredient alone or together with a pharmaceutically acceptable carrier. The daily dosage of the active ingredient depends on age and the individual condition, and on the method of administration.

The novel pharmaceutical preparations contain, for example, from approximately 10% to approximately 80%, preferably from approximately 20% to approximately 60%, of active ingredient. Pharmaceutical preparations according to the invention for enteral or parenteral administration are, for example, those in dosage unit forms, such as dragées, tablets, capsules or suppositories, and also ampoules. These are manufactured in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture and processing the mixture or granulate, if desired or necessary after the addition of suitable adjuncts, to form tablets or dragée cores.

Suitable carriers are especially fillers, such as sugar, for example lactose, saccharose, mannitol or sorbitol, cellulose preparations and/or calcium phosphates, for example tricalcium phosphate or calcium biphosphate, also binders, such as starch pastes using, for example corn, wheat, rice or potato starch, gelatine, tragacanth, methylcellulose and/or polyvinylpyrrolidone, and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores are provided with suitable coatings that are optionally resistant to gastric juices, there being used, inter alia, concentrated sugar solutions which may contain gum arabic, talc, polyvinylpyrrolidone, polyethylene glycol and/or titanium dioxide, lacquer solutions in suitable organic solvents or solvent mixtures or, for the production of coatings that are resistant to gastric juices, solutions of suitable cellulose preparations, such as acetylcellulose phthalate or hydroxypropylmethylcellulose phthalate. Dyes or pigments can be added to the tablets or dragée coatings, for example for identification purposes or to indicate different doses of active ingredient.

Further pharmaceutical preparations for oral administration are dry-filled capsules consisting of gelatine and also soft, sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also to add stabilisers.

As rectally administrable pharmaceutical preparations there come into consideration, for example, suppositories which consists of a combination of the active ingredient with a suppository base. Suitable suppository bases are, for example, natural or synthetic triglycerides, paraffin hydrocarbons, polyethylene glycols and higher alkanols. It is also possible to use gelatine rectal capsules which contain a combination of the active ingredient with a base material; as base materials there come into consideration, for example, liquid triglycerides, polyethylene glycols and paraffin hydrocarbons.

Especially suitable for parenteral administration are aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain substances which increase the viscosity, for example sodium carboxymethylcellulose, sorbitol and/or dextran, and, optionally, also stabilisers.

There come into consideration as pharmaceutical preparations for topical use especially creams, ointments, pastes, foams, tinctures and soutions that contain from approximately 0.1% to approximately 5% of active ingredient.

Creams are oil-in-water emulsions that contain more than 50% of water. As oily base there are used especially fatty alcohols, for example lauryl, cetyl or stearyl alcohol, fatty acids, for example palmitic or stearic acid, liquid to solid waxes, for example isopropyl myristate, wool waxes or beeswax, and/or hydrocarbons, for example petroleum jelly (petrolactum) or paraffin oil. As emulsifiers there come into consideration surface-active substances having predominantly hydrophilic properties, such as corresponding non-ionic emulsifiers, for example fatty acid esters of polyalcohols, or ethylene oxide adducts thereof, such as polyglycerine fatty acid esters or polyoxyethylene sorbitan fatty acid esters (Tweens), also polyoxyethylene fatty alcohol ethers or polyoxyethylene fatty acid esters, or corresponding ionic emulsifiers, such as alkali metal salts of fatty alcohol sulphates, for example sodium lauryl sulphate, sodium cetyl sulphate or sodium stearyl sulphate, which are customarily used in the presence of fatty alcohols, for example cetyl alcohol or stearyl alcohol. Additives to the aqueous phase are, inter alia, agents that reduce the drying out of the creams, for example polyalcohols, such as glycerine, sorbitol, propylene glycol and/or polyethylene glycols, also preservatives, perfumes etc..

Ointments are water-in-oil emulsions that contain up to 70%, but preferably from approximately 20% to approximately 50%, of water of aqueous phases. As fatty phase there come into consideration especially hydrocarbons, for example petroleum jelly, paraffin oil and/or hard paraffins, which, in order to improve the water-binding capacity, preferably contain suitable hydroxy compounds, such as fatty alcohols or esters thereof, for example cetyl alcohol or wool wax alcohols, or wool waxes. Emulsifiers are corresponding lipophilic substances, such as sorbitan fatty acid esters (Spans), for example sorbitan oleate and/or sorbitan isostearate. Additives to the aqueous phase are, inter alia, humectants, such as polyalcohols, for example glycerine, propylene glycol, sorbitol and/or polyethylene glycol, and also preservatives, perfumes etc..

Fatty ointments are anhydrous and contain as base especially hydrocarbons, for example paraffin, petroleum jelly and/or liquid paraffins, and also natural or partially synthetic fats, for example coconut fatty acid triglyceride, or preferably hardened oils, for example hydrogenated ground nut oil or castor oil, and also fatty acid partial esters of glycerine, for example glycerine mono- and di-stearate, and also, for example, the fatty alcohols, which increase the water-absorbing capacity, emulsifiers and/or additives mentioned in connection with the ointments.

Pastes are creams and ointments containing powder ingredients that absorb secretions, such as metal oxides, for example titanium oxide or zinc oxide, also talc and/or aluminium silicates, the purpose of which is to bind any moisture or secretions present.

Foams are administered, for example, from pressurised containers and are liquid oil-in-water emulsions in aerosol form, halogenated hydrocarbons, such as chlorofluoro-lower alkanes, for example dichlorodifluoromethane and dichlorotetrafluoroethane, being used as propellants. For the oily phase there are used, inter alia, hydrocarbons, for example paraffin oil, fatty alcohols, for example cetyl alcohol, fatty acid esters, for example isopropyl myristate, and/or other waxes. As emulsifiers there are used, inter alia, mixtures of those emulsifiers having predominantly hydrophilic properties, such as polyoxyethylene sorbitan fatty acid esters (Tweens), and those having predominantly lipophilic properties, such as sorbitan fatty acid esters (Spans). In addition, there may be used customary additives, such as preservatives etc..

Tinctures and solutions generally have an aqueous ethanolic base to which there are added, inter alia, polyalcohols, for example glycerine, glycols, and/or polyethylene glycol, as humectants for reducing evaporation, and fat-restoring substances, such as fatty acid esters with lower polyethylene glycols, that is to say lipophilic substances that are soluble in the aqueous mixture, to replace the fatty substances that are taken from the skin by the ethanol, and, if necessary, other adjuncts and additives.

The pharmaceutical preparations for topical application are manufactured in a manner known per se, for example by dissolving or suspending the active ingredient in the base or, if necessary, in a part thereof. When processing the active ingredient in the form of a solution, it is usually dissolved in one of the two phases before emulsification; when processing the active ingredient in the form of a suspension, it is mixed with a part of the base after emulsification and then added to the remainder of the formulation.

The dosage of the active ingredient depends on the species of warm-blooded animal, age and individual condition, and on the method of administration. In normal cases, the estimated approximate daily dose in the case of oral administration to a warm-blooded animal weighing approximately 75 kg is from approximately 100 to approximately 600 mg, advantageously divided into several equal partial doses.

The following Examples illustrate the invention described above but are not intended to limit the scope of the invention in any way. Temperatures are given in degrees Centigrade.

EXAMPLE 1

A mixture of 18.2 g (0.1 mole) of 4-methyl-3-(3-oxobutyl)-maleic acid anhydride and 17.5 g (0.15 mole) of dimethylammonium benzoate in 400 ml of benzene is heated under reflux using a water separator for 42 hours. The benzene is removed in vacuo and the residue that remains is partitioned between methylene chloride and saturated sodium bicarbonate solution. The crude product remaining after drying and after removal of the methylene chloride is chromatographed over silica gel with petroleum ether/ether. Subsequent recrystallisation from ether/petroleum ether yields 6-dimethylamino-3-methylbenzofuran-2(3H)-one having a melting point of from 87° to 89° C.

The starting material can be produced as follows.

A hot solution of 80 g (2 moles) of sodium hydroxide solution in 200 ml of water is added in portions, while stirring, to a mixture of 341 g (2 moles) of the hydrochloride of imidazo[1,2-a]pyridin-2(3H)-one in 700 ml of water. Subsequently, a solution of 250.7 g (2.16 moles) of maleic acid in 600 ml of water is added dropwise in such a manner that the internal temperature of the reaction mixture remains between 40° and 45° C. After 30 hours at room temperature (20° to 25° C.), the mixture is cooled to 5° C., the resulting precipitate is filtered off, the filtrate is concentrated in vacuo to approximately half its volume and the resulting product is filtered with suction. The combined residues are washed with a little cold methanol and dried in vacuo at 50° C. There are obtained 400 g of 3-(1,2-dicarboxyethyl)-imidazo[1,2a]pyridin-2(3H)-one having a melting point of 193° C. (decomposition). The resulting product is stirred at room temperature for 6 hours with 650 ml of concentrated hydrochloric acid. After cooling to 5° C., the precipitate is filtered off, the filtrate is concentrated in vacuo to approximately half its volume and the resulting product is filtered with suction. The combined residues are washed with acetone and dried in vacuo at 50° C. In this manner the hydrochloride of 3-(1,2-dicarboxyethyl)-imidazo[1,2-a]pyridin-2(3H)-one having a melting point of 205° C. (decomposition) is obtained.

A mixture of 18.9 g (0.066 mole) of the hydrochloride of 3-(1,2-dicarboxyethyl)-imidazo[1,2-a]pyridin-2(3H)-one, 7 g (0.1 mole) of methyl vinyl ketone, 50 ml of methanol and 50 ml of water is stirred at room temperature for 36 hours. The product is then precipitated by the dropwise addition of approximately 15 ml of 4N aqueous sodium hydroxide solution. The precipitate is filtered with suction, washed with water, methanol and acetone and dried in vacuo at 50° C. 8 g (38% of the theoretical yield) of 3-(1,2-dicarboxyethyl)-3-(3-oxobutyl)-imidazo[1,2-a]pyridin-2(3H)-one having a melting point of 195° C. (decomposition) are obtained.

A mixture of 114.7 g (0.4 mole) of the hydrochloride of 3-(1,2-dicarboxyethyl)-midazo[1,2-a]pyridin-2(3H)-one, 36.4 g (0.52 mole) of methyl vinyl ketone, 150 ml of methanol and 150 ml of water is stirred at room temperature for 36 hours and then concentrated to dryness by evaporation in vacuo at approximately 45° C. The resulting crude product is taken up in 300 ml of glacial acetic acid, 15 g of sodium acetate are added and the mixture is boiled under reflux until $CO_2$ evolution is complete. Then, the solvent is removed in vacuo, a mixture of 150 ml of 6M sulphuric acid and 150 ml of tetrahydrofuran is added to the residue, and the whole is maintained at 60° C. for 8 hours. After removing the tetrahydrofuran in vacuo, the reaction mixture is diluted with water, extracted with methylene chloride and filtered through silica gel. Distillation of the crude product in a high vacuum (115° C. to 125° C./8 Pa) yields 4-methyl-3-(3-oxobutyl)-maleic acid anhydride as a spectroscopically homogeneous pale yellow oil. For elemental analysis a sample is chromatographed over silica gel with petroleum ether/diethyl ether.

EXAMPLE 2

In a manner analogous to that described in Example 1, using as starting materials 4-methyl-3-(3-oxobutyl)-maleic acid anhydride and methyl-2-butylammonium benzoate, 6-(N-methyl-N-2-butylamino)-3-methylbenzofuran-2(3H)-one is obtained in the form of a colourless oil, b.p. $_{0.005}$, 140° C.

EXAMPLE 3

In a manner analogous to that described in Example 1, using as starting materials 4-methyl-3-(3-oxobutyl)-maleic acid anhydride and dicyclopropylmethylammonium benzoate, 6-dicyclopropylmethylamino-3-methylbenzofuran-2(3H)-one is obtained in the form of a colourless oil, b.p. $_{0.005}$, 200° C.

EXAMPLE 4

A cold solution of chlorine in chloroform is added dropwise at 0° to 5° C., while stirring, to a mixture of 14.7 g (0.063 mole) of 3-methyl-6-(N-methyl-N-2-butylamino)-benzofuran-2(3H)-one in 100 ml of chloroform until no more educt is visible in the thin layer chromatograph. The reaction mixture is washed with methylene chloride, dilute sodium bicarbonate solution and water. The crude product remaining after drying and concentration by evaporation of the organic phase is chromatographed over silica gel with petroleum ether/ether. Recrystallisation of the pure fractions from ether/petroleum ether yields 5-chloro-3-methyl-6-(N- methyl-N-2-butylamino)-benzofuran-2(3H)-one in the form of a colourless oil, b.p. $_{0.05}$, 190° C.

EXAMPLE 5

In a manner analogous to that described in Example 4, using as starting materials 6-dicyclopropylmethylamino-3-methyl-2(3H)-benzofuran-2(3H)-one and chlorine, 5-chloro-6-dicyclopropylmethylamino-3-methylbenzofuran-2(3H)-one is obtained in the form of a colourless oil, b.p. $_{0.005}$, 240° C.

EXAMPLE 6

20 g of 2-(4-dibenzylamino-2-hydroxy-5-methylphenyl)-propionic acid dibenzylamide are heated under reflux for 3 hours in 40 ml of 2N hydrochloric acid and 40 ml of glacial acetic acid. The mixture is then concentrated to dryness by evaporation in vacuo and the residue is partitioned between ether and 1N sodium hydroxide solution. Acidification to a pH of 1 with hydrochloric acid and extraction yields 2-(4-dibenzylamino-2-hydroxy-5-methylphenyl)-propionic acid which, for purification, is chromatographed over silica gel in methylene chloride. The colourless crystals melt at 174°–175°. 15 g of the crystals are dissolved in 50 ml of ether and 6 g of dicyclohexylcarbodiimide are added thereto. After 30 minutes the urea formed is filtered off and the filtrate is concentrated to dryness by evaporation. In this manner 6-dibenzylamino-3,5-dimethylbenzofuran-2(3H)-one having a melting point of 122°–123° is obtained.

The starting material can be produced as follows.

A mixture of 172 g (0.6 mole) of the hydrochloride of 3-(1,2-dicarboxyethyl)-imidazo[1,2-a]pyridin-2(3H)-one, 65.5 g (0.78 mole) of 3-methyl-3-buten-2-one, 220 ml of methanol and 220 ml of water is stirred at room temperature for 36 hours and then concentrated to dryness by evaporation in vacuo at approximately 45°. The resulting crude product is taken up in 400 ml of glacial acetic acid, 22.5 g of sodium acetate are added, and the mixture is boiled under reflux until $CO_2$ evolution is complete. The solvent is then removed in vacuo, a mixture of 225 ml of 6M sulphuric acid and 225 ml of tetrahydrofuran is added to the residue, and the mixture is heated under reflux for 8 hours. After removing tetrahydrofuran in vacuo, the reaction mixture is diluted with water and extracted with methylene chloride. The crude product remaining after drying and concentrating by evaporation the organic phase is chromatographed over silica gel with petroleum ether/ether. The subsequent distillation (100° C./$8.10^{-2}$ torr) yields 4-methyl-3-(2-methyl-3-oxobutyl)-maleic acid anhydride in the form of a pale yellow oil.

59 g of 4-methyl-3-(2-methyl-3-oxobutyl)-maleic acid anhydride and 240 g of dibenzylammonium benzoate are boiled under reflux for 48 hours in 1000 ml of benzene using a water separator. The mixture is then concentrated to dryness by evaporation in vacuo and the residue is chromatographed over silica gel. The resulting oil crystallises from isopropyl ether. In this manner 2-(4-dibenzylamino-2-hydroxy-5-methylphenyl)-propionic acid dibenzamide having a melting point of 140°–141° is obtained.

EXAMPLE 7

Tablets containing 100 mg of active ingredient, for example 6-dimethylamino-3-methylbenzofuran-2(3H)-one, are manufactured as follows:

| Composition (for 1000 tablets): | |
| --- | --- |
| active ingredient | 100.0 g |
| lactose | 248.5 g |
| corn starch | 17.5 g |
| polyethylene glycol 6000 | 5.0 g |
| talc | 15.0 g |
| magnesium stearate | 4.0 g |
| demineralised water | q.s. |

MANUFACTURE

The solid ingredients are first of all forced through a sieve having a mesh width of 0.6 mm. Then, the active ingredient, lactose, talc, magnesium stearate and half the starch are intimately mixed. The other half of the starch is suspended in 65 ml of water and this suspension is added to a boiling solution of the polyethylene glycol in 260 ml of water. The resulting paste is added to the pulverulent substances, and the whole is mixed and granulated, if necessary with the addition of water. The granulate is dried overnight at 35° C., forced through a sieve having a mesh width of 1.2 mm and compressed to form tablets approximately 10 mm in diameter that are concave on both sides and have a break notch on the upper side.

EXAMPLE 8

Chewing tablets containing 30 mg of active ingredient, for example 3-methyl-6-(N-methyl-N-2-butylamino)-benzofuran-2(3H)-one can be manufactured, for example, as follows:

| Composition (for 1000 tablets) | |
| --- | --- |
| active ingredient | 30.0 g |
| mannitol | 267.0 g |
| lactose | 179.5 g |
| talc | 20.0 g |
| glycine | 12.5 g |
| stearic acid | 10.0 g |
| saccharin | 1.0 g |
| 5% strength gelatine solution | q.s. |

MANUFACTURE

All of the solid ingredients are first of all forced through a sieve having a mesh width of 0.25 mm. The mannitol and the lactose are mixed, granulated with the addition of gelatine solution, forced through a sieve having a mesh width of 2 mm, dried at 50° C., and forced through a further sieve having a mesh width of 1.7 mm. The active ingredient, the glycine and the saccharin are carefully mixed, the mannitol, the lactose granulate, the stearic acid and the talc are added, and the whole is thoroughly mixed and compressed to form tablets approximately 10 mm in diameter that are concave on both sides and have a break groove on the upper side.

EXAMPLE 9

Tablets containing 25 mg of active ingredient, for example 5-chloro-6-dicyclopropylmethylamino-3-methylbenzofuran-2(3H)-one can be manufactured as follows:

| Constituents (for 1000 tablets): | |
| --- | --- |
| active ingredient | 25.0 g |

| Constituents (for 1000 tablets): | |
|---|---|
| lactose | 100.7 g |
| wheat starch | 7.5 g |
| polyethylene glycol 6000 | 5.0 g |
| talc | 5.0 g |
| magnesium stearate | 1.8 g |
| demineralised water | q.s. |

MANUFACTURE

All of the solid ingredients are first of all forced through a sieve having a mesh width of 0.6 mm. Then, the active ingredient, the lactose, the talc, the magnesium stearate and half the starch are mixed. The other half of the starch is suspended in 40 ml of water and this suspension is added to a boiling solution of the polyethylene glycol in 100 ml of water. The resulting starch paste is added to the main mixture which is then granulated, if necessary with the addition of water. The granulate is dried overnight at 35° C., forced through a sieve having a mesh width of 1.2 mm and compressed to form tablets having a diameter of approximately 6 mm that are concave on both sides.

We claim:

1. A benzofuranone of the formula

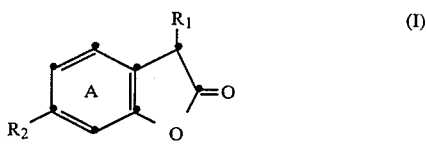

in which $R_1$ represents hydrogen or lower alkyl, $R_2$ represents an amino group di-substituted by two lower alkyl groups which are unsubstituted or substituted by 3- to 7-membered cycloalkyl, by unsubstituted phenyl or by phenyl substituted by lower alkyl, lower alkenyl, lower alkylene, hydroxy-lower alkyl, halogeno-lower alkyl, lower alkoxy, lower alkylthio, lower alkanesulphinyl, lower alkanesulphonyl, hydroxy, halogen, lower alkanoyloxy, lower alkanoyl and/or nitro, and the aromatic ring A is unsubstituted or additionally substituted by lower alkyl, hydroxy-lower alkyl, halogeno-lower alkyl, lower alkenyl, 3- to 4-membered alkylene having 3 to 8 carbon atoms, lower alkoxy, lower alkylthio, lower alkanesulphinyl, lower alkanesulphonyl, hydroxy, halogen, lower alkanoyloxy, lower alkanoyl and/or nitro, or a pharmaceutically acceptable salt or tautomer thereof.

2. A compound of the formula (I) according to claim 1, in which $R_1$ represents hydrogen or lower alkyl, $R_2$ represents a di-lower alkylamino group, a dicycloalkyl-lower alkylamino group having 3 to 7 ring members in each cycloalkyl moiety, or a diphenyl-lower alkylamino group each phenyl moiety of which is unsubstituted or substituted by lower alkyl, lower alkoxy, hydroxy, halogen, lower alkanoyloxy and/or trifluoromethyl, and the aromatic ring A is unsubstituted or additionally substituted by lower alkyl, lower alkoxy, hydroxy, halogen, lower alkanoyloxy, 3- or 4-membered alkylene and/or trifluoromethyl, or a pharmaceutically acceptable salt or tautomer thereof.

3. A compound according to claim 1, wherein the formula has the following structure

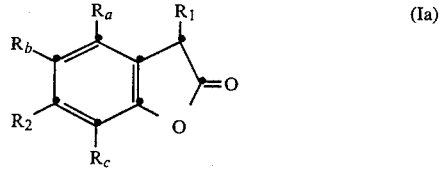

in which $R_1$ represents hydrogen or, lower alkyl, and $R_2$ represents di-lower alkylamino, dicycloalkyl-lower alkylamino having 3 to 7 ring members in each cycloalkyl moiety, or diphenyl-lower alkylamino each phenyl moiety of which is unsubstituted or substituted by lower alkyl, lower alkoxy, hydroxy, halogen, lower alkanoyloxy and/or trifluoromethyl and $R_a$, $R_b$ and $R_c$ each represents, independently of one another, hydrogen, lower alkyl, lower alkoxy, hydroxy, halogen, lower alkanoyloxy, or trifluoromethyl or a pharmaceutically acceptable salt and or tautomer thereof.

4. A compound of the formula (Ia) according to claim 3, in which $R_1$ is hydrogen, $R_2$ represents di-lower alkylamino having up to and including 4 carbon atoms in each lower alkyl moiety, $R_a$ and $R_c$ represent hydrogen and $R_b$ represents lower alkyl having up to and including 4 carbon atoms or halogen having an atomic number up to and including 35, or a pharmaceutically acceptable salt or tautomer thereof.

5. A compound of the formula (Ia) according to claim 3, in which $R_1$ represents lower alkyl having up to and including 4 carbon atoms, $R_2$ represents di-lower alkylamino having up to and including 4 carbon atoms in each lower alkyl moiety, $R_a$ and $R_c$ represent hydrogen, and $R_b$ represents lower alkyl having up to and including 4 carbon atoms or halogen having an atomic number up to and including 35 or a pharmaceutically acceptable salt or tautomer thereof.

6. A compound according to claim 1 being 5-chloro-3-methyl-6-(N-methyl-N-2-butyl-amino)-benzofuran-2(3H)-one or a pharmaceutically acceptable salt or tautomer thereof.

7. A compound according to claim 1 being 5-chloro-6-dicyclopropylmethylamino-3-methylbenzofuran-2(3H)-one or a pharmaceutically acceptable salt or tautomer thereof.

8. A compound according to claim 1 being 6-dimethylamino-3-methyl-benzofuran-2(3H)-one or a pharmaceutically acceptable salt thereof.

9. A compound according to claim 1 being 6-dibenzylamino-3,5-dimethyl-benzofuran-2(3H)-one or a pharmaceutically acceptable salt thereof.

10. A pharmaceutical composition comprising an antiinflammatory and analgesically effective amount of a compound as claimed in claim 1 or a pharmaceutically acceptable salt or tautomer thereof together with a pharmaceutical adjunct or carrier.

11. A method for treating inflammation and pain in warm-blooded animals comprising treating warm-blooded animals with a pharmaceutically effective amount of a compound as claimed in claim 1 or a pharmaceutically acceptable salt or isomer thereof.

* * * * *